United States Patent
Karpf et al.

US 6,437,171 B1
Aug. 20, 2002

(54) PROCESS FOR PREPARING 1,2-DIAMINO COMPOUNDS

(75) Inventors: Martin Karpf, Reinach; René Trussardi, Birsfelden, both of (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/590,317

(22) Filed: Jun. 8, 2000

(30) Foreign Application Priority Data

Jun. 11, 1999 (EP) .......................................... 99111418
Feb. 21, 2000 (EP) .......................................... 00103588

(51) Int. Cl.$^7$ ..................... C07C 227/08; C07C 247/14; C07D 317/44
(52) U.S. Cl. ..................... 560/125; 560/128; 560/169; 549/436; 549/546; 549/961
(58) Field of Search .................. 560/125, 128; 560/169; 549/436, 546, 961

(56) References Cited

U.S. PATENT DOCUMENTS

| 5,763,483 A | 6/1998 | Bischofberger et al. |
| 5,859,284 A | 1/1999 | Kent et al. |
| 5,866,601 A | 2/1999 | Lew et al. |
| 5,886,213 A | 3/1999 | Kent et al. |
| 5,952,375 A | 9/1999 | Bischofberger et al. |
| 5,994,377 A | 11/1999 | Kim et al. |
| 6,057,459 A | 5/2000 | Kent et al. |

FOREIGN PATENT DOCUMENTS

| FR | 1559511 | * | 3/1969 |
| WO | WO 96/26933 | | 9/1996 |
| WO | WO 98/07685 | | 2/1998 |
| WO | WO 98 07685 | * | 2/1998 |
| WO | WO 99/14185 | | 3/1999 |

OTHER PUBLICATIONS

Yamamoto et al. "Regio–and stereo–selective ring opening of epoxides with amide cuprate reagents.", J. Chem. Soc., Chem. Commun. 1993, pp. 1201–1203.*
C. U. Kim, et al., J. Am. Chem. Soc. 1997, vol. 119, pp. 681–690.
J.C. Rohloff, et al., J. Org. Chem. 1998, vol. 63, pp. 4545–4550.
Green, T., Protective Groups in Organic Synthesis, Chapter 7, John Wiley & Sons, Inc. 1991, pp. 315–385.
M. Chini, et al., Tetrahedron Lett. 1994, vol. 35, pp. 433–436.
P. Van de Weghe, Tetrahedron Lett. 1995, vol. 36, pp. 1649–1652.
Y. Yamamoto, J. Chem. Soc., Chem. Commun. 1993, pp. 1201–1203.
M. Caron, et al., J. Org. Chem. 1985, vol. 50, pp. 1557–1560.
Müller, et al., J. Org. Chem. 1998, vol. 63, pp. 9753–9755.
Advanced Organic Chemistry, ed. March J. John Wiley & Sons, New York, 1992 pp. 353–357.
Dobrev et al., Tetrahedron Letters, No. 39, pp. 4013–4016 (1972).
Fülöp et al., J. Org. Chem., vol. 58, pp. 1967–1969 (1969).
Abstract #164618y for C10.

* cited by examiner

*Primary Examiner*—Ralph Gitomer
*Assistant Examiner*—Devesh Khare
(74) *Attorney, Agent, or Firm*—George W. Johnston; Dennis P. Tramaloni

(57) ABSTRACT

The invention provides a multistep process for preparing 1,2-diamino compounds of formula

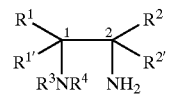

I wherein $R^1$, $R^{1'}$, $R^2$, $R^{2'}$, $R^3$ and $R^4$ have the meaning given in the specification and pharmaceutically acceptable addition salts thereof, from 1,2-epoxides of formula

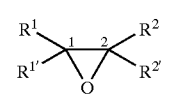

II wherein $R^1$, $R'$, $R^2$ and $R^{2'}$ have the meaning given in the specification.

41 Claims, No Drawings

PROCESS FOR PREPARING 1,2-DIAMINO COMPOUNDS

BACKGROUND OF THE INVENTION

The present invention concerns a new multi-step process for preparing 1,2-diamino compounds from 1,2-epoxides, in particular 1,2-diamino compounds useful as inhibitors of viral or bacterial neuraminidases, a new step of that multi-step process for preparing 2-aminoalcohols from 1,2-epoxides, a new step for the transformation of a 2-aminoalcohol into a 1,2-diamino compound as well as specific intermediates useful in that multi-step process.

PCT Patent Publication No. 96/26933 describes a large class of compounds useful as inhibitors of viral or bacterial neuraminidases and their preparation. These compounds comprise a six membered partially unsaturated carbocyclic or heterocyclic ring system, which can be substituted by several different substituents.

PCT Patent Publication No. 98/07685 discloses various methods for preparing compounds of the above class which are cyclohexene carboxylate derivatives. A particularly interesting compound is (3R,4R,5S)-5-amino-4-acetylamino-3-(1-ethyl-propoxy)-cyclohex-1-ene-carboxylic acid ethyl ester (C. U. Kim et al., J. Am.Chem. Soc., 1997, 119, 681–690). A method of preparation of that 1,2-diamino compound in 10 steps starting from shikimic acid, or in 12 steps starting from quinic acid, is described by J. C. Rohloff et al., J. Org. Chem.,1998, 63, 4545–4550. The 10 step method involves a final 4-step reaction sequence from the 1,2-epoxide (1S,5R,6R)-5-(1-ethyl-propoxy)-7-oxa-bicyclo[4.1.0]hept-3-ene-3-carboxylic acid ethyl ester via three potentially highly toxic and explosive azide intermediates. Dedicated know-how and expensive equipment are required to perform such a process. In a technical process it is preferable to avoid use of azide reagents and azide intermediates.

The problem to be solved by the present invention therefore was to find an azide-free process for preparing 1,2-diamino compounds from 1,2-epoxides.

That problem has been solved by the invention as described below and as defined in the appended claims.

SUMMARY OF THE INVENTION

The invention provides a process for preparing 1,2-diamino compounds of formula

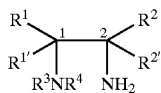

I and pharmaceutically acceptable addition salts thereof wherein, $R^1$, $R^{1'}$, $R^2$ and $R^{2'}$, independently of each other, are H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, aryl-lower alkyl, aryl-lower alkenyl, or aryl-lower alkynyl, or $R^1$ and $R^2$, $R^1$ and $R^{2'}$, $R^{1'}$ and $R^2$ or $R^{1'}$ and $R^{2'}$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, with the proviso that at least one of $R^1$, $R^{1'}$, $R^2$ and $R^{2'}$ is not H, and $R^3$ and $R^4$, independently from each other, are H or a substituent of an amino group, with the proviso that not both $R^3$ and $R^4$, are H, which process is characterized in that it comprises the steps of a) reacting a 1,2-epoxide of formula

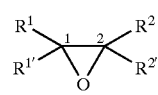

II wherein $R^1$, $R^{1'}$, $R^2$ and $R^{2'}$ are as above with an amine of formula $R^5NHR^6$ wherein $R^5$ and $R^6$, independently of each other, are H, or a substituent of an amino group, with the proviso that not both $R^5$ and $R^6$ are H to form a 2-aminoalcohol of formula

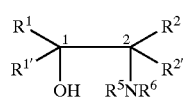

III wherein $R^1$, $R^{1'}$, $R^2$, $R^{2'}$, $R^5$ and $R^6$ are as above b) converting the 2-aminoalcohol of formula (III) into a 2-aminoalcohol of formula

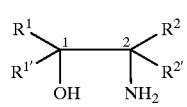

IV wherein $R^1$, $R^{1'}$, $R^2$ and $R^{2'}$ are as above, c) transforming the 2-aminoalcohol of formula (IV) into a 1,2-diamino compound of formula

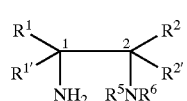

V wherein $R^1$, $R^{1'}$, $R^2$, $R^{2'}$, $R^5$ and $R^6$ are as above d) acylating the free amino group in position 1 of the 1,2-diamino compound of formula (V) to form an acylated 1,2-diamino compound of formula

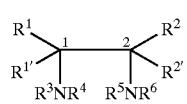

VI wherein $R^1$, $R^{1'}$, $R^2R^{2'}$, $R^3$, $R^4$, $R^5$ and $R^6$ are as above and finally e) deprotecting the amino group in position 2 of formula (VI) to form the 1,2-diamino compound of formula (I).

If desired, the resulting 1,2-diamino compound of formula (I) can be further transformed into a pharmaceutically acceptable addition salt.

DETAILED DESCRIPTION OF THE INVENTION

The term "alkyl" means a straight chain or branched saturated alkyl group with 1–20, preferably 1–12, C-atoms, which can carry one or more substituents.

The term "alkenyl" means a straight chain or branched alkenyl group with 2–20, preferably 2–12, C-atoms, which can carry one or more substituents.

The term "alkynyl" means a straight chain or branched alkynyl group with 2–20, preferably 2–12, C-atoms, which can carry one or more substituents.

The term "cycloalkyl" signifies a saturated, cyclic hydrocarbon group with 3–12, preferably 5–7, C-atoms, which can carry one or more substituents.

The term "aryl" denotes a mono-nuclear or di-nuclear aromatic group which can carry one or more substituents, such as, for example, phenyl, substituted phenyl, naphthyl, or substituted naphthyl.

The term "heterocyclyl" means a saturated or unsaturated monocyclic or bicyclic group with 1 or 2 nitrogen, sulfur and/or oxygen atoms such as, for example pyranyl, dihydropyranyl, tetrahydropyranyl, thiopyranyl, isobenzofuranyl, furanyl, tetrahydrofuranyl, thiofuranyl, dihydrothiofuranyl, benzo[b]dihydrofuranyl, tetrahydrothiofuranyl, thioxanyl, dioxanyl, dithianyl, chromanyl, isochromanyl, dithiolanyl, pyridyl, pyperidyl, imidazolidinyl, pyrrolidinyl, quinolyl or isoquinolyl, which can carry one or more substituents.

The term "carbocyclic ring system" means a cyclic alkyl group with 3–12, preferably 5–7, C-atoms, which can include one or two carbon-carbon double bonds, and which can carry one or more substituents, such as for example cyclopentene, substituted cyclopentene, cyclohexene, substituted cyclohexene, cycloheptene, or substituted cycloheptene.

The term "heterocyclic ring system" means a monocyclic or bicyclic group with 1 or 2 nitrogen, sulfur and/or oxygen atoms, which can include one or two double bonds and carry one or more substituents, as exemplified above under the term "heterocyclyl", for example tetrahydropyran, dihydropyran, substituted dihydropyran, tetrahydrofuran, isobenzotetrahydrofuran, thioxan, 1,4-dioxane, dithian, dithiolan, piperidine, or piperazine.

Suitable substituents on the above groups are those which are inert in the reactions involved.

Examples of suitable substituents on such alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, or aryl-lower alkyl, aryl-lower alkenyl, aryl-lower alkynyl, are lower alkyl, lower alkoxy, lower alkyl carboxylate, carboxylic acid, carboxamide, N-(mono/di-lower alkyl)-carboxamide.

Examples of suitable substituents on such a carbocyclic or heterocyclic ring system are alkyl of 1 to 12 C-atoms, alkenyl of 2 to 12 C-atoms, alkynyl of 2 to 12 C-atoms, alkoxy of 1 to 12 C-atoms, alkyl of 1 to 12 C-atoms-carboxylate, carboxylic acid, carboxamide, N-(mono/di-alkyl of 1 to 12 C-atoms)-carboxamide. Preferred substituents are lower alkyl, lower alkenyl, lower alkynyl, lower alkoxy, carboxylic acid, lower alkyl carboxylate, carboxamide, N-(mono/di-lower alkyl)-carboxamide.

The term "lower" here denotes a group with 1–6, preferably 1–4, C-atoms. Examples of lower alkyl groups are methyl, ethyl, n-propyl, isopropyl, n-butyl, isobutyl, sec.-butyl, tert.-butyl, pentyl and its isomers and hexyl and its isomers. Examples of lower alkoxy groups are methoxy, ethoxy, propoxy, isopropoxy, n-butoxy, iso-butoxy, sec.-butoxy, tert.-butoxy and 1-ethyl-propoxy. Examples of lower alkyl carboxylates are methyl carboxylate, ethyl carboxylate, propyl carboxylate, isopropyl carboxylate and butyl carboxylate. Examples of lower alkanoyl groups are acetyl, propionyl and butyryl.

In accordance with the present invention, the term "substituent of an amino group" refers to any substituents conventionally used to hinder the reactivity of an amino group, as described in Green, T., "Protective Groups in Organic Synthesis", Chapter 7, John Wiley and Sons, Inc., 1991, 315–385, herein incorporated by reference. Such preferred substituents are acyl, alkyl, alkenyl, alkynyl, aryl-lower alkyl, silyl methyl wherein silyl is trisubstituted with lower alkyl, lower alkenyl, lower alkynyl and/or aryl. Advantageously the reactivity of the amino group can also be hindered by protonation e.g. with Lewis acids, including $H^+$.

The term "acyl" means alkanoyl, preferably lower alkanoyl, alkoxy-carbonyl, preferably lower alkoxy-carbonyl, aryloxy-carbonyl or aroyl such as benzoyl.

In a preferred embodiment the invention comprises a process for preparing 4,5-diamino-shikimic acid derivatives of formula

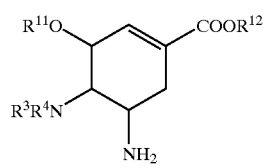

VII and pharmaceutically acceptable addition salts thereof wherein
$R^{11}$ is an optionally substituted alkyl group, $R^{12}$ is an alkyl group and $R^3$ and $R^4$ independently of each other, are H or a substituent of an amino group, with the proviso that not both $R^3$ and $R^4$ are H
from a cyclohexene oxide of formula

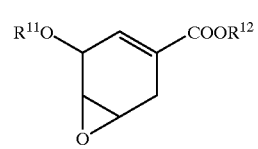

VIII wherein $R^{11}$ and $R^{12}$ are as above.

The term alkyl in $R^{11}$ has the meaning of a straight chain or branched alkyl group of 1 to 20 C-atoms, expediently of 1 to 12 C-atoms. Examples of such alkyl groups are methyl, ethyl, n-propyl, i-propyl, n-butyl, i-butyl, tert.-butyl, pentyl and its isomers, hexyl and its isomers, heptyl and its isomers, octyl and its isomers, nonyl and its isomers, decyl and its isomers, undecyl and its isomers and dodecyl and its isomers.

This alkyl group can be substituted with one or more substituents as defined in e.g. WO 98/07685. Suitable substituents are alkyl having 1 to 20 C-atoms(as defined above), alkenyl having 2 to 20 C-atoms, cycloalkyl having 3 to 6 C-atoms, hydroxy, alkoxy having 1 to 20 C-atoms, alkoxy-carbonyl having 1 to 20 C-atoms, F, Cl, Br, and J.

The preferred meaning for $R^{11}$ is 1-ethylpropyl.

$R^{12}$ here is a straight chain or branched alkyl group of 1 to 12 C-atoms, expediently of 1 to 6 C-atoms as exemplified above.

The preferred meaning for $R^{12}$ is ethyl.

In the compound of formula (VII), the substituent of an amino group is as defined above Suitable substituents of amino groups are also described in, e.g., the WO 98/07685.

Preferred substituents of an amino group for $R^3$ and $R^4$ are alkanoyl groups, more preferably lower-alkanoyl with 1 to 6 C-atoms such as hexanoyl, pentanoyl, butanoyl (butyryl), propanoyl (propionyl), ethanoyl (acetyl) and methanoyl (formyl). Preferred alkanoyl group and therefore preferred meaning for $R^3$ is acetyl and for $R^4$ is H.

The most preferred 1,2-diamino compound of formula (I) or 4,5-diamino-shikimic acid derivative of formula (VII) therefore is the (3R,4R,5S)-5-amino-4-acetylamino-3-(1-ethyl-propoxy)-cyclohex-1-ene-carboxylic acid ethyl ester or the (3R,4R,5S)-5-amino-4-acetylamino-3-(1-ethyl-propoxy)-cyclohex-1-ene-carboxylic acid ethyl ester phosphate (1:1). The most preferred 1,2-epoxide of formula (II) or cyclohexene oxide of formula (VIII) therefore is the (1S,5R,6R)-5-(1-ethyl-propoxy)-7-oxa-bicyclo[4.1.0]hept-3-ene-3-carboxylic acid ethyl ester.

Step a)

Step a) comprises reacting a 1,2-epoxide of formula (II) with an amine of formula $R^5NHR^6$ to form the respective 2-aminoalcohol of formula (III).

The amine of formula $R^5NHR^6$ of step (a) is a primary or secondary amine which shows reactivity for opening the 1,2-epoxide ring.

$R^5$ and $R^6$ in the amine of formula $R^5NHR^6$ expediently is a straight chain or branched alkenyl of 2 to 6 C-atoms, optionally substituted benzyl or tri-substituted silyl methyl or heterocyclyl methyl.

The straight chain or branched alkenyl of 2 to 6 C-atoms preferably is allyl or an analog thereof such as allyl or an allyl group which is substituted on the α, β-or γ-carbon by one lower alkyl, lower alkenyl, lower alkynyl or aryl group. Suitable examples are, e.g., 2-methylallyl, 3,3-dimethylallyl, 2-phenylallyl, or 3-methylallyl. Preferred amines of formula $R^5NHR^6$ with the meaning of a straight chain or branched alkenyl of 1 to 6 C-atoms group therefore are allylamine, diallylamine or 2-methylallylamine, whereby allylamine is the most preferred.

Optionally substituted benzyl preferably is benzyl or benzyl analogs which are either substituted on the α-carbon atom with one or two lower alkyl, lower alkenyl, lower alkynyl or aryl groups or substituted on the benzene ring with one or more lower alkyl, lower alkenyl, lower alkynyl, lower-alkoxy or nitro groups. Suitable examples are α-methylbenzyl, α-phenylbenzyl, 2-methoxybenzyl, 3-methoxybenzyl, 4-methoxybenzyl, 4-nitrobenzyl or 3-methylbenzyl. Preferred amines of formula $R^5NHR^6$ with the meaning of an optionally substituted benzyl group are benzylamine, dibenzylamine, methylbenzylamine, 2-methoxybenzylamine, 3-methoxybenzylamine or 4-methoxybenzylamine, whereby benzylamine is the most preferred.

Trisubstituted silyl methyl preferably is silyl methyl trisubstituted with aryl, lower alkyl, lower alkenyl and/or lower alkynyl groups. Suitable examples are trimethylsilyl, triethylsilyl, diphenylmethylsilyl, phenyldimethylsilyl or tert.-butyldimethylsilyl. Preferred amine of formula $R^5NHR^6$ with the meaning of tri-substituted silyl methyl is the trimethylsilyl methylamine.

Heterocyclyl methyl preferably is heterocyclyl methyl wherein either the methyl group is substituted with one or two lower alkyl, lower alkenyl, lower alkynyl or aryl groups or the heterocyclic ring is substituted with one or more lower alkyl, lower alkenyl, lower alkynyl or lower alkoxy groups. Suitable examples are furfuryl or picolyl.

The most preferred amine of formula $R^5NHR^6$ is allylamine.

The amine of formula $R^5NHR^6$ is generally used in a molar amount of 1.0 to 3.0 equivalents, preferably of 1.5 to 2.5 equivalents, based on one equivalent of the 1,2-epoxide of formula (II).

Step (a) can be performed without a catalyst under normal or elevated pressure, however, the reaction time of step (a) can in general be significantly reduced in the presence of a catalyst.

Suitably the catalyst is a metal catalyst or a magnesium halide.

Convenient metal catalysts known to catalyze ring opening reactions of 1,2-epoxides with amines e.g. are lanthanide compounds such as lanthanide trifluoromethanesulfonates like $Yb(OTf)_3$, $Gd(OTf)_3$ and $Nd(OTf)_3$ (M. Chini et al., Tetrahedron Lett., 1994, 35, 433–436), samarium iodides (P. Van de Weghe, Tetrahedron Lett., 1995, 36, 1649–1652) or other metal catalysts such as amide cuprate reagents (Y. Yamamoto, J. Chem. Soc., Chem. Commun., 1993, 1201–1203) and $Ti(O-i-Pr)_4$ (M. Caron et al., J. Org. Chem., 1985, 50, 1557 and M. Müller, et al., J. Org. Chem., 1998, 68, 9753).

As a rule the ring opening with metal catalysts is carried out in the presence of an inert solvent e.g. in tetrahydrofuran at temperatures between 20° C. and 150° C.

In accordance with the present invention, the magnesium halides are the preferred catalysts for the ring opening of 1,2-epoxides with amines. The term "magnesium halide derivative" here denotes anhydrous or hydrated magnesium chloride, magnesium bromide or magnesium iodide, or an etherate, in particular a dimethyl etherate, a diethyl etherate, a dipropyl etherate, or a diisopropyl etherate thereof.

Magnesium bromide diethyl etherate is the most preferred catalyst.

The magnesium halide is suitably used in a molar amount of 0.01 to 2.0 equivalents, preferably of 0.15 to 0.25 equivalents, based on one equivalent of the 1,2-epoxide of formula (II).

Suitable solvents for the magnesium halide catalysis are protic solvents such as ethanol or methanol, or preferably an aprotic solvent such as tetrahydrofuran, dioxane, tert.-butyl methyl ether, diisopropylether, isopropylacetate, ethylacetate, methylacetate, acetonitrile, benzene, toluene, pyridine, methylene chloride, dimethylformamide, N-methylformamide and dimethylsulfoxide or mixtures thereof.

The aprotic solvent is preferably selected from tetrahydrofuran, diisopropylether, tert.-butyl methyl ether, acetonitrile, toluene or a mixture thereof, most preferably is a mixture of tert.-butyl methyl ether and acetonitrile.

Magnesium halide catalysis is advantageously carried out at temperatures between 0° C. and 200° C., preferably between 50° C. and 150° C.

The respective 2-aminoalcohol of formula (III) can after the reaction has been finished be isolated and if so desired purified by methods known to those skilled in the art.

Step b)

Step b) comprises converting the 2-aminoalcohol of formula (III) into a 2-aminoalcohol of formula (IV).

The conversion in step b), is dependent on the residue $R^5$ and $R^6$.

If $R^5$ and $R^6$ independently of each other are straight chain or branched alkenyl of 2 to 6 C-atoms, the conversion is an isomerization/hydrolysis performed in the presence of a metal catalyst.

If $R^5$ and $R^6$ independently of each other are optionally substituted benzyl or heterocyclyl methyl, the conversion is a hydrogenolysis performed with hydrogen in the presence of a metal catalyst; or If $R^5$ and $R^6$ independently of each other are tri-substituted silyl methyl, the conversion is an oxidative cleavage.

The fact that the preferred meaning for $R^5$ and $R^6$ are straight chain or branched alkenyl of 2 to 6 C-atoms as outlined above at step a) isomerization/hydrolysis is the preferred method for the conversion in step b).

Isomerization/hydrolysis accordingly takes place in the presence of a suitable metal catalyst, expediently a precious metal catalyst such as Pt, Pd or Rh either applied on an inert support such as charcoal or alumina, or in complexed form. A preferred catalyst is 5 to 10% palladium on carbon (Pd/C).

The catalyst is suitably used in an amount of 2 to 30 wt. %, preferably, 5 to 20 wt. % relating to the 2-aminoalcohol of formula (III).

The isomerization/hydrolysis is advantageously carried out in an aqueous solvent. The solvent itself can be protic or aprotic. Suitable protic solvents are e.g. alcohols such as methanol, ethanol or isopropanol. Suitable aprotic solvent is e.g. acetonitrile or dioxane.

The reaction temperature is preferably chosen in the range of 20° C. and 150° C.

It was found that isomerization/hydrolysis is preferably effected in the presence of a primary amine.

Primary amines suitably used are ethylenediamine, ethanolamine, or suitable derivatives of these primary amines mentioned hereinbefore. A particularly interesting primary amine is ethanolamine.

The primary amine is suitably used in an amount of 1.0 to 1.25 equivalents, preferably of 1.05 to 1.15 equivalents relating to the 2-aminoalcohol of formula (III).

As mentioned above, if $R^5$ and $R^6$ are, independently, optionally substituted benzyl or heterocyclyl methyl, the conversion is a hydrogenolysis performed in the presence of a metal catalyst with hydrogen. Hydrogenolysis conditions are well known in the art and described e.g. in Green, T., "Protective Groups in Organic Synthesis", Chapter 7, John Wiley and Sons, Inc.,1991, 364–365.

Hydrogenolysis accordingly takes place in the presence of a suitable metal catalyst, expediently a precious metal catalyst such as Pt, Pd or Rh either applied on an inert support such as charcoal or alumina, or in complexed form. A preferred catalyst is 5 to 10% palladium on carbon (Pd/C). The catalyst is suitably used in an amount of 2 to 30 wt. %, preferably 5 to 20 wt. % relating to the 2-aminoalcohol of formula (III).

Hydrogenolysis advantageously is carried out in an aqueous solvent. The solvent itself can be protic or aprotic. Suitable protic solvents are, e.g., alcohols such as methanol, ethanol or isopropanol. Suitable aprotic solvents are, e.g., acetonitrile or dioxane. The reaction temperature is preferably chosen in the range of 20° C. and 150° C.

As mentioned above, if $R^5$ and $R^6$, independently of each other, are tri-substituted silyl methyl, the conversion is an oxidative cleavage.

Expediently the reaction is performed in the presence of a haloimide.

Haloimides suitable for this reaction are N-chlorosuccinimide, N-bromosuccinimide or N-chlorobenzene sulfonamide (chloramine-T).

The reaction can be performed in the presence of an inert solvent at temperatures of 20° C. to 150° C.

In order to completely hydrolyze any imines that may have formed in step b) the reaction mixture is usually treated with an acid e.g. with sulfuric acid or hydrochloric acid.

Step c)

Step c) comprises the transformation of the 2-aminoalcohol of formula (IV) into a 1,2-diamino compound of formula (V)

In detail step c) comprises the steps, (c1) protecting the free amino group of the 2-aminoalcohol of formula (IV) with a substituent of an amino group;

(c2) activating the hydroxy group into a leaving group, and (c3) deprotecting the amino group and treating the reaction product with an amine of formula $R^5NHR^6$, wherein $R^5$ and $R^6$ are as above to form a 1,2-diamino compound of formula (V).

Step c1)

In accordance with the present invention, the term "substituent of an amino group" refers to a substituent conventionally used to hinder the reactivity of the amino group. As stated above, suitable substituents are described in Green T., "Protective Groups in Organic Synthesis", Chapter 7, John Wiley and Sons, Inc.,1991, 315–385.

Particularly interesting is the conversion of the amino group with a carbonyl group containing compound to form an imine, a so called "Schiff base".

Also acyl substituents which are formed by treating of the 2-aminoalcohol of formula (IV) with an acylating agent may be utilized to hinder the reactivity of the amino group.

Formation of a Schiff base is the preferred method for the conversion of the free amino group of the 2-aminoalcohol of formula (IV) into a substituted amino group.

Carbonyl compounds suitable to form a Schiff base are either aldehydes or ketones. Both the aldehydes and the ketones can be aliphatic, alicyclic or aromatic, preferably aromatic.

Examples of suitable aliphatic aldehydes are propionaldehyde, 2-methylpentenal, 2-ethylbutyraldehyde, pivaldehyde, ethyl glyoxylate and chloral. An example of an alicyclic aldehyde is cyclopropan carbaldehyde. Examples of suitable aromatic aldehydes are furfural, 2-pyridinecarboxylaldehyde, 4-methoxybenzaldehyde, 3-nitrobenzaldehyde, a benzaldehyde sulfonate, a furfural sulfonate, and benzaldehyde. A particularly interesting aromatic aldehyde is benzaldehyde.

Examples of suitable aliphatic ketones are 1,1-dimethoxyacetone and 1,1-diethoxyacetone. Examples of suitable alicyclic ketones are cyclopentanone, cyclohexanone, cycloheptanone, 2-ethyl cyclohexanone and 2-methyl-cyclopentanone. An example of an aromatic ketone is acetophenone.

A preferred carbonyl containing compound is benzaldehyde.

The carbonyl containing compound is expediently used in an amount of 1.0 to 1.50, preferably 1.10 to 1.40 equivalents relating to the 2-aminoalcohol of formula (IV).

Formation of the Schiff base is advantageously performed in a protic or aprotic solvent, preferably in an aprotic solvent.

Suitable aprotic solvents are for example tetrahydrofuran, dioxane, tert.-butyl methyl ether, diisopropylether, isopropylacetate, ethylacetate, methylacetate, acetonitrile, benzene, toluene, pyridine, methylene chloride, dimethylformamide, N-methylformamide and dimethylsulfoxide. A preferred aprotic solvent is tert.-butyl methyl ether.

The water formed is usually removed by azeotropic distillation.

Formation of the Schiff base is advantageously carried out at temperatures between 30° C. and 180° C., preferably between 60° C. and 140° C.

If step c1) comprises acylation, as mentioned above, the 2-aminoalcohol of formula (IV) is transformed into a 2-acyl aminoalcohol.

The acylating agent can be a carboxylic acid, or an activated derivative thereof, such as an acyl halide, a carboxylic acid ester or a carboxylic acid anhydride. Suitable acylating agents are acetylchloride, trifluoracteylchloride, benzoyl chloride or acetic anhydride. A preferred acyl group is formyl. Suitable formylating agent therefore is e.g. a formic acid mixed anhydride such as for example formic acid acetic acid anhydride, or a formic acid ester, such as ethyl formate or methyl formate or a formic acid active ester such as cyanomethyl formate.

The acylating agent is suitably used in an amount of 1.0 to 1.3, preferably 1.1 to 1.2 equivalents relating to the 2-aminoalcohol of formula (IV).

The choice of solvent is not critical as long as it does not interfere with the reactants. It was found that e.g. ethylacetate is a suitable solvent. The reaction can however also be performed without solvent i.e. in the presence of the respective acylating agent applied in excess.

Reaction temperature usually is in the range of –20° C. to 100° C.

Step c2)

Step (c2) comprises activating the hydroxy group into a leaving group, thereby forming an O-substituted 2-aminoalcohol.

Compounds and methods for effecting this transformation are well known in the art and described e.g. in "Advanced Organic Chemistry", ed. March J., John Wiley & Sons, New York, 1992, 353–357.

It was found that the hydroxy group is preferably transformed into a sulfonic acid ester by treating the hydroxy group with a sulfonylating agent.

Agents commonly used for producing sulfonic acid esters e.g. are the halogenides or the anhydrides of the following sulfonic acids: methane sulfonic acid, p-toluenesulfonic acid, p-nitrobenzenesulfonic acid, p-bromobenzenesulfonic acid or trifluoromethanesulfonic acid.

Preferred sulfonylating agents are halogenides or anhydrides of methane sulfonic acid such as methane sulfonylchloride.

The sulfonylating agent is expediently added in an amount of 1.0 to 2.0 equivalents relating to one equivalent of the 2-aminoalcohol of formula (IV).

Preferably, the reaction in step c2) takes place in an inert solvent, more preferably, in the same solvent which has been used in the previous step c1) and at a reaction temperature of –20° C. to 100° C.

Step (c3)

Step (c3) comprises deprotecting the amino group, i.e., cleaving the substituent of the amino group. Any conventional method and conditions for cleaving the substituent of the amino group can be utilized. These conditions also remove the leaving group which results in the formation of an aziridine intermediate of formula

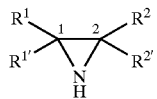    IX wherein $R^1$, $R^{1'}$, $R^2$ and $R^{2'}$ are as above.

This aziridine intermediate can be isolated, but preferably, is reacted in situ with an amine of formula $R^5NHR^6$, wherein $R^5$ and $R^6$ are as defined above, to form the 1,2-diamino compound of formula (V).

The amine of formula $R^5NHR^6$ is the very same as applied in step a). Also the same preferences are applicable as for the amine in step a). Accordingly the most preferred amine of formula $R^5NHR^6$ used for step c3) is allylamine.

The course of the reaction in step c3) and the respective reaction conditions mainly depend on the kind of protection of the amino group in step c2).

Having a Schiff base the transformation is directly effected with the amine of formula $R^5NHR^6$, whereby having an acetyl group, prior to the transformation with the amine of formula $R^5NHR^6$ a deacylation treatment has to take place first.

In case of a Schiff base, the amine of formula $R^5NHR^6$ is used in an amount of at least two equivalents, preferably of 2.0 to 5.0, more preferably of 2.5 to 4.0 equivalents relating to one equivalent of the 2-aminoalcohol of formula (IV).

The solvent used in this reaction step (c3) is as a rule the same as of the previous step c2). Accordingly protic or aprotic solvents, preferably aprotic solvents, such as for example tetrahydrofuran, dioxane, tert.-butyl methyl ether, diisopropylether, isopropylacetate, ethylacetate, methylacetate, acetonitrile, benzene, toluene, pyridine, methylene chloride, dimethylformamide, N-methylformamide and dimethylsulfoxide can be used. A preferred solvent is tert.-butyl methyl ether.

In case of a Schiff base the conversion is advantageously carried out at a temperature of 60° C. to 170° C., preferably of 90° C. to 130° C. and applying normal pressure to 10 bars.

When the substituted amino group is acyl, prior to the treatment with the amine of formula $R^5NHR^6$, deacylation has to take place as mentioned above.

Deacylation can easily be effected under acidic conditions, e.g., using sulfuric acid, methanesulfonic acid or p-toluenesulfonic acid.

Thereby the respective sulfonate or sulfate salt of the O-substituted 2-aminoalcohol is formed.

The amine of the formula $R^5NHR^6$ is then suitably used in an amount of 1.0 to 5.0 equivalents, preferably of 2.0 to 4.0 equivalents relating to one equivalent of the 2-aminoalcohol of formula (IV).

The choice of solvents is about the same as for the conversion of the Schiff base, preferably ethyl acetate or tert.-butyl methyl ether.

The reaction temperature is chosen between 60° C. and 170° C., preferably between 90° C. and 130° C. and the pressure is selected between normal pressure and 10 bar.

When operating with a Schiff base step c) thus can efficiently be performed in a one pot synthesis without isolating the intermediates.

Step d)

Step d) comprises the acylation of the free amino group in position 1 of the 1,2-diamino compound of formula (V) to form an acylated 1,2-diamino compound of formula (VI).

Acylation can be effected under strong acidic conditions by treating the 1,2-diamino compound of formula (V) with acylating agents known to the skilled in the art. The acylating agent can be an aliphatic or aromatic carboxylic acid, or an activated derivative thereof, such as an acyl halide, a carboxylic acid ester or a carboxylic acid anhydride. Suitable acylating agents are preferably acetylating agents such as acetylchloride, trifluoracteylchloride or acetic anhydride. A suitable aromatic acylating agent is benzoylchloride. Strong acids suitably used e.g. are mixtures of methane sulfonic acid and acetic acid or sulfuric acid and acetic acid.

Acylation however can also take place under non-acidic conditions using e.g. N-acetyl imidazole or N-acetyl-N-methoxy acetamide.

Preferably however the acylation takes place under acidic conditions using a mixture of 0.5 to 2.0 equivalents of acetic anhydride, 0 to 15.0 equivalents of acetic acid and 0 to 2.0 equivalents of methanesulfonic acid in ethyl acetate.

An inert solvent such as tert.-butyl methyl ether may be added, it is however also possible to run the reaction without addition of any solvent.

The temperature is as a rule chosen in the range of −20° C. to 100° C.

Step e)

Step e) comprises deprotecting the amino group in position 2 and, if desired, further transforming the resulting 1,2-diamino compound of formula (I) into a pharmaceutically acceptable addition salt.

Deprotecting the amino group, i.e., removal of the substituent of the amino group in position 2 takes place following the same methods and applying the same conditions as described in step b).

The conversion in step e), accordingly is also dependent on the residue $R^5$ and $R^6$. Therefore, if $R^5$ and $R^6$ independently of each other are straight chain or branched alkenyl of 2 to 6 C-atoms, the conversion is a hydrolysis performed in the presence of a metal catalyst, if $R^5$ and $R^6$ independently of each other are optionally substituted benzyl or heterocyclyl methyl, the conversion is a hydrogenolysis performed with hydrogen in the presence of a metal catalyst or if $R^5$ and $R^6$ independently of each other is tri-substituted silyl methyl, the conversion is an oxidative cleavage.

The same preferences as for step b) are valid for step e). For any further details reference is made to step b).

As a rule the 1,2-diamino compound of formula (I) can be isolated e.g. by evaporation and crystallization, but it is preferably kept in e.g. an ethanolic solution and then further transformed into a pharmaceutically acceptable addition salt following the methods described in J. C.Rohloff et al., J.Org.Chem.,1998, 63, 4545–4550; WO 98/07685).

The term "pharmaceutically acceptable acid addition salts" embraces salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methane sulfonic acid, p-toluenesulfonic acid and the like.

The salt formation is effected in accordance with methods which are known per se and which are familiar to any person skilled in the art. Not only salts with inorganic acids, but also salts with organic acids come into consideration. Hydrochlorides, hydrobromides, sulfates, nitrates, citrates, acetates, maleates, succinates, methansulfonates, p-toluenesulfonates and the like are examples of such salts.

Preferred pharmaceutically acceptable acid addition salt is the 1:1 salt with phosphoric acid which can be formed preferably in ethanolic solution at a temperature of −20° C. to 50° C.

The invention also relates to the following new intermediates:

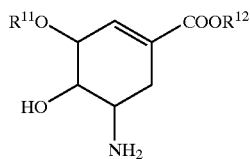

X wherein $R^{11}$ and $R^{12}$ are as stated above, or an addition salt thereof.

A preferred representative of the compounds of formula (X) is (3R,4S,5R)-5-amino-3-(1-ethyl-propoxy)-4-hydroxy-cyclohex-1-ene carboxylic acid ethylester ($R^{11}$=1-ethyl-propyl, $R^{12}$=ethyl)

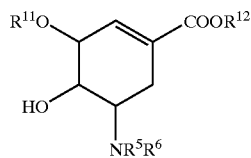

XI wherein $R^5$, $R^6$, $R^{11}$ and $R^{12}$ are as stated above, or an addition salt thereof.

Preferred representatives of compounds of formula (XI) are (3R,4S,5R)-5-allylamino-3-(1-ethylpropoxy)-4-hydroxy-cyclohex-1-ene carboxylic acid ethylester (with $R^{11}$=1-ethyl-propyl, $R^{12}$=ethyl, $R^5$=H and $R^6$=allyl) and (3R,4R,5R)-5-formylamino-3-(1-ethylpropo)-4-hydroxy-cyclohex-1-en carboxylic acid ethylester (with $R^{11}$=1-ethylpropyl, $R^{12}$=ethyl, $R^5$=H and $R^6$=formyl)

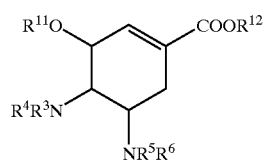

XII wherein $R^3$, $R^4$, $R^5$, $R^6$, $R^{11}$ and $R^{12}$ are as stated above or an addition salt thereof.

Preferred representatives of compounds of formula (XII) are (3R,4R,5S)-4-acetylamino-5-allylamino-3-(1-ethylpropoxy)-cyclohex-1-ene carboxylic acid ethylester (with $R^{11}$=1-ethyl propyl, $R^{12}$=ethyl, $R^5$=H, $R^6$=allyl, $R^3$=H, $R^4$=acetyl) and (3R,4R,5S)-4-amino-5-allylamino-3-(1-ethylpropoxy)-cyclohex-1-en carboxylic acid ethyl ester (with $R^{11}$=1-ethylpropyl, $R^{12}$=ethyl, $R^5$=H, $R^6$=allyl, $R^3$=H, $R^4$=H)

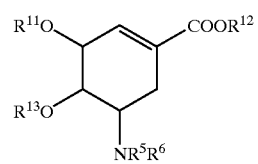

XIII wherein $R^5$, $R^6$, $R^{11}$ and $R^{12}$ are as stated above and $R^{13}$ is a sulfonyl group, or an addition salt thereof.

Preferred representatives of compounds of formula (XIII) are (3R,4R,5R)-5-formylamino-4-methanesulfonyl-3-(1-ethylpropoxy)-cyclohex-1-ene carboxylic acid ethylester (with $R^{11}$=1-ethylpropyl, $R^{12}$=ethyl, $R^5$=H, $R^6$=formyl, $R^{13}$=methanesulfonyl) and (3R,4R,5R)-5-amino-4-methanesulfonyl-3-(1-ethylpropoxy)cyclohex-1-en carboxylic acid ethylester methansulfonate (1:1) (with $R^{11}$=1-ethylpropyl, $R^{12}$=ethyl, $R^5$=H, $R^6$=H, $R^{13}$=methanesulfonyl)

The invention also relates to a new process for preparing a 2-aminoalcohol of formula

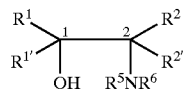

III wherein $R^1$, $R^{1'}$, $R^2$ and $R^{2'}$, independently from each other, are H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, or aryl-lower alkyl, aryl-lower alkenyl, aryl-lower alkynyl, or $R^1$ and $R^2$, $R^1$ and $R^{2'}$, $R^{1'}$ and $R^2$ or $R^{1'}$ and $R^{2'}$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, with the proviso that at least one of $R^1$, $R^{1'}$, $R^2$ and $R^{2'}$ is not H, and $R^5$ and $R^6$, independently of each other, are H or a substituent of an amino group, with the proviso that not both $R^5$ and $R^6$ are H, comprising treating a 1,2-epoxide of formula

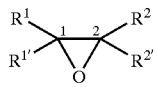

II wherein $R^1$, $R^{1'}$, $R^2$ and $R^{2'}$ are as above with an amine of formula $R^5NHR^6$ wherein $R^5$ and $R^6$ are as above in the presence of a magnesium halide catalyst.

This process corresponds to the preferred method of step a) as described herein before. Accordingly the respective description of step a) is incorporated herein by reference.

A preferred amine of formula $R^5NHR^6$ accordingly is allylamine, diallylamine, benzylamine, dibenzylamine or trimethylsilyl amine more preferably allylamine and preferred magnesium halide catalyst is magnesium bromide diethyl etherate.

The invention further relates to a new process for the transformation of the 2-aminoalcohol of formula (IV)

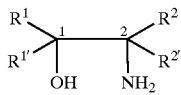

IV wherein $R^1$, $R^{1'}$, $R^2$ and $R^{2'}$ are as above, into a 1,2-diamino compound of formula (V)

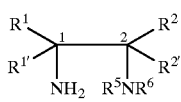

V wherein $R^1$, $R^{1'}$, $R^2$, $R^{2'}$, $R^5$ and $R^6$ are as above.

This process corresponds to step c) as described herein before. Accordingly the whole description of step c) is incorporated herein by reference. Also the same preferences as given under c) apply here.

As stated above, this process comprises the steps, (c1) protecting the free amino group of the 2-aminoalcohol of formula (IV) with a substituent of an amino group;

(c2) activating the hydroxy group into a leaving group, and (c3) deprotecting the amino group and treating the reaction product with an amine of formula $R^5NHR^6$, wherein $R^5$ and $R^6$ are as above into a 1,2-diamino compound of formula (V).

In a preferred embodiment this process is characterized by c1) forming a Schiff base by reacting the 2-aminoalcohol of formula (IV) with a carbonyl group containing compound, preferably with benzaldehyde, c2) treating the hydroxy group with a sulfonylating agent to form a sulfonic acid ester, preferably, a methanesulfonic acid ester, and c3) deprotecting the amino group of the 2-aminoalcohol of formula (IV) to form an aziridine intermediate, and treating the aziridine intermediate with allylamine, diallylamine, benzylamine, dibenzylamine or trimethylsilyl amine, preferably with allylamine to form the 1,2-diamino compound of formula (V).

The invention is further illustrated by the following examples.

EXAMPLE 1

Preparation of (3R,4R,5S)-5-amino-4-acetylamino-3-(1-ethyl-propoxy)-cyclohex-1-ene-carboxylic acid ethyl ester from (1S,5R,6R)-5-(1-ethyl-propoxy)-7-oxa-bicyclo[4.1.0]hept-3-ene-3-carboxylic acid ethyl ester (a) Preparation of (3R,4S,5R)-5-allylamino-3-(1-ethyl-propoxy)-4-hydroxy-cyclohex-1-enecarboxylic acid ethyl ester In a 2.5 l 4-necked round bottom flask equipped with a reflux condenser, a thermometer, a mechanical stirrer and an inert gas supply 254.3 g (1.0 mol) of (1S,5R,6S)-5-(1-ethyl-propoxy)-7-oxa-bicyclo[4.1.0]hept-3-ene-3-carboxylic acid ethyl ester were dissolved under argon with stirring in 900 ml tert.-butyl methyl ether and 100 ml acetonitrile whereby the temperature dropped to about 10° C. To the clear, yellowish solution 51.7 g (0.2 mol) of magnesium bromide diethyl etherate were added followed by 150 ml (2.0 mol) of allylamine whereby the temperature rose to about 20° C. The yellow suspension was heated to 55° C. whereby complete dissolution occurred after about 1.5 h. The clear yellow solution was refluxed for 15 h. The yellowish, turbid solution was cooled to about 30° C. and stirred vigorously with 1000 ml of 1M aqueous ammonium sulfate for 15 min whereby a clear two-phase mixture evolved after initial cloudiness. The organic phase was separated, filtered and evaporated in a rotary evaporator at 48° C./340 mbar to a volume of about 580 ml. The solid particles were filtered and the brown solution was evaporated at 48° C./340 to 15 mbar for 2 h to yield as the crude product 312.8 g (97%) of (3R,4S,5R)-5-allylamino-3-(1-ethyl-propoxy)-4-hydroxy-cyclohex-1-enecarboxylic acid ethyl ester as a brown-yellow oil containing about 7.0% of the 4-allylamino-5-hydroxy isomer.

IR (film): 2966, 1715, 1463, 1244, 1095 cm$^{-1}$; MS (EI, 70eV): 311 (M$^+$), 280, 240, 210, 99 m/z.

(b) Preparation of (3R,4S,5R)-5-amino-3-(1-ethyl-propoxy)-4-hydroxy-cyclohex-1-enecarboxylic acid ethyl ester In a 2.5 l 4-necked round bottom flask equipped with a reflux condenser, a thermometer, a mechanical stirrer and an inert gas supply 312.8 g of (3R,4S,5R)-5-allylamino-3-(1-ethyl-propoxy)-4-hydroxy-cyclohex-1-enecarboxylic acid ethyl ester obtained according to (a) were dissolved at room temperature and stirring under argon in 1560 ml of ethanol.

To the clear, dark yellow solution were added 66.2 ml of ethanolamine (d=1.015, 1.10 mol) and 31.3 g of palladium on charcoal 10%. The black suspension was heated to 78° C. in the course of 25 min and refluxed for 3 h. The suspension was cooled below 40° C., filtered through a filter paper and the filter cake was washed with 100 ml of ethanol. The combined orange filtrates were cooled to 0 to 5° C., treated with 59.0 ml of sulfuric acid (d=1.83, 1.10 mol) keeping the temperature below 30° C. The yellow suspension (pH=2.5) was evaporated in a rotary evaporator at 48° C./160 to 50 mbar and the remaining oily, yellow crystals (956 g) were dissolved in 1000 ml of deionized water and the orange solution was extracted with a mixture of 500 ml of tert.-butyl methyl ether and 500 ml of n-hexane. The organic phase was extracted with 260 ml of 0.5M aqueous sulfuric acid and the combined aqueous phases (pH=2.3) were cooled to 10° C. and treated with stirring with about 128 ml of 50% aqueous potassium hydroxide until pH=9.5 was reached keeping the temperature in the range of 5° C. to 20° C. The organic phase was separated and the aqueous phase was extracted first with 1000 ml, then twice with 500 ml, in total with 2000 ml of tert.-butyl methyl ether. The combined organic extracts were dried over 1000 g of sodium sulfate and filtered. The filter cake was washed with about 300 ml of tert.-butyl methyl ether and the combined filtrates were evaporated in a rotary evaporator at 48° C./360 to 20 mbar and dried at 48° C./15 mbar for 2 h to yield crude (3R,4S,5R)-5-amino-3-(1-ethyl-propoxy)-4-hydroxy-cyclohex-1-enecarboxylic acid ethyl ester (271.4 g) as a red oil containing about 4% of the 4-amino-5-hydroxy isomer.

IR (film): 2966, 1715, 1463, 1247, 1100 cm$^{-1}$; MS (EI, 70eV): 280 (M$^+$), 240, 183, 138, 110 m/z.

(c1) Preparation of (3R,4R,5S)-5-allylamino-4-amino-3-(1-ethyl-propoxy)-cyclohex-1-enecarboxylic acid ethyl ester In a 4 l 4-necked round bottom flask equipped with Dean-Stark trap, a thermometer, a mechanical stirrer and an inert gas supply 271.4 g of (3R,4S,5R)-5-amino-3-(1-ethyl-propoxy)-4-hydroxy-cyclohex-1-enecarboxylic acid ethyl ester obtained according to (b) were dissolved at room temperature and stirring under argon in 2710 ml of tert.-butyl methyl ether. The red solution was treated with 102.1 ml of benzaldehyde (d=1.05, 1.01 mol) and heated at reflux for 2 h during which time about 9 ml of water separated. In the course of 30 min 1350 ml of tert.-butyl methyl ether were distilled. The red solution containing the intermediate was cooled to 0° C.–5° C. and treated with 167.3 ml of triethylamine (d=0.726,1.18 mol). Then 77.7 ml of methanesulfonyl chloride (d=1.452, 0.99 mol) were added dropwise keeping the temperature in the range of 0° C. to 5° C. in the course of 85 min during which time an orange precipitate formed. After stirring for 45 min without cooling HPLC analysis showed about 15% of the intermediate (3R, 4R, 5S)-5-(benzylidene-amino)-4-hydroxy-cyclohex-1-enecarboxylic acid ethyl ester. After dropwise addition of 7.8 ml of methanesulfonyl chloride (d=1.452, 0.09 mol) at room temperature and stirring for 10 min HPLC analysis showed about 8% of the above intermediate. After dropwise addition at room temperature of 7.8 ml of methanesulfonyl chloride (d=1.452, 0.09 mol) and stirring for 15 min HPLC analysis showed less than 1% of that intermediate. The orange suspension was filtered and the yellow-orange filter cake was washed with 300 ml of tert.-butyl methyl ether. The combined filtrates (1291 g) containing the intermediate (3R, 4R, 5S)-5-(benzylidene-amino)-4-mesyloxy-cyclohex-1-ene carboxylic acid ethyl ester were treated with 300.5 ml of allylamine (d=0.76, 4.0 mol) and the clear red solution was heated in a 3 l autoclave under 1 bar of argon with stirring to 110° C.–111° C. in the course of 45 min, then stirred at this temperature and at a pressure of 3.5 to 4.5 bar for 15 h, cooled to less than 45° C. during 1 h. The red solution was evaporated in a rotary evaporator at 48° C./600 to 10 mbar and the remaining red gel (566 g) was dissolved with intensive stirring in a two phase mixture of 1000 ml of 2N hydrochloric acid and 1000 ml of ethyl acetate. The organic phase was extracted with 1000 ml of 2N hydrochloric acid, the combined aqueous phases were washed with 500 ml of ethyl acetate, cooled to 10° C. and treated with stirring with about 256 ml of 50% aqueous potassium hydroxide until pH=10.1 was reached keeping the temperature in the range of 10° C. to 20° C. The organic phase was separated and the aqueous phase was extracted first with 1000 ml, then with 500 ml, in total with 1500 ml of tert.-butyl methyl ether and the combined extracts were evaporated in a rotary evaporator at 48° C./340 to 10 mbar to yield crude (3R,4R,5S)-5-allylamino-4-amino-3-(1-ethyl-propoxy)-cyclohex-1-enecarboxylic acid ethyl ester (277.9 g) as a red-brown oil.

IR (film): 2966, 1715, 1463, 1244, 1090 cm$^{-1}$; MS (EI, 70eV): 310 (M), 222, 136, 98 m/z.

(c2) Preparation of (1R,5R,6S)-2-{[3-ethoxycarbonyl-5-(1-ethyl-propoxy)-6-hydroxycyclohex-3-enylimino]-methyl}-benzenesulfonic acid sodium salt To a stirred suspension of 27.1 g (100 mmol) (3R,4S,5R)-5-amino-3-(1-ethylpropoxy)-4-hydroxycyclohexene-1-carboxylic acid ethyl ester and 20.8 g (100 mmol) 2-formylbenzenesulfonic acid sodium salt in 270 ml ethanol was heated to reflux under argon for 2 hours. The brown, turbid reaction mixture was evaporated in a rotary evaporator and the residue was treated twice with 135 ml of ethyl acetate and evaporated in a rotary evaporator at 50° C. to dryness to yield 45.88 g (99%) of (1R,5R,6S)-2-{[3-ethoxycarbonyl-5-(1-ethyl-propoxy)-6-hydroxy-cyclohex-3-enylimino]-methyl}-benzenesulfonic acid sodium salt as a yellow amorphous solid. IR (film): 3417, 2924, 2726, 1714, 1638, 1464, 1378, 1237, 1091, 970 cm$^{-1}$; MS (ISP-MS): 438.3 (M$^+$–Na) m/z.

Preparation of (3R,4S,5R)-5-amino-3-(1-ethyl-propoxy)-4-methanesulfonyloxy-cyclohex-1-enecarboxylic acid ethyl ester To a stirred suspension of 9.23 g (20 mmol) (1R,5R,6S)-2-{[3-ethoxycarbonyl-5-(1-ethyl-propoxy)-6-hydroxy-cyclohex-3-enylimino]-methyl}-benzenesulfonic acid sodium salt and 3.50 ml (25 mmol) of triethylamine in 90 ml ethyl acetate was added 1.80 ml (23 mmol) methanesulfonyl chloride at to 0 to 5° C. The resulting brown-yellowish suspension was stirred at room temperature for 2 hours, treated with 2.70 ml (40 mmol) ethylenediamine and after 10 min with 90 ml of water. After stirring the 2-phase system vigorously for 1 hour the organic phase was separated and extracted with 100 ml water and 3 times with 100 ml aqueous 1M NaHCO$_3$ solution, dried over Na$_2$SO$_4$, filtered and evaporated in a rotary evaporator at 48° C./4 mbar to dryness to yield 6.36 g (91%) of (3R,4S,5R)-5-amino-3-(1-ethyl-propoxy)-4-methanesulfonyloxy-cyclohex-1-enecarboxylic acid ethyl ester as an orange oil. An analytical sample of was obtained by column chromatography on silica gel using t-BuOMe containing 1% of 25% ammonia as the eluent. IR (film): 2966, 2936, 2878, 1711, 1653, 1463, 1351, 1246, 1172, 1068, 961 cm$^{-1}$; MS (EI, 7o eV)): 350 (M$^+$), 262, 224, 182, 166, 136 m/z.

Preparation of (1R,5R,6S) 5-(1-Ethyl-propoxy)-7-aza-bicyclo[4.1.0]hept-3-ene-3-carboxylic acid ethyl ester A yellowish solution of 0.87 g (2.5 mmol) (3R,4S,5R)-5-amino-3-(1-ethyl-propoxy)-4-methanesulfonyloxy-cyclohex-1-enecarboxylic acid ethyl ester and 0.17 ml (2.5 mmol) of ethylenediamine in 4.4 ml ethanol was heated to reflux for 1 hour. The resulting suspension was evaporated in a rotary evaporator to dryness and the residue was suspended in 5 ml ethyl acetate, extracted with 2 ml aqueous 1M NaHCO$_3$ solution, dried over Na$_2$SO$_4$, filtered and evaporated in a rotary evaporator at reduced pressure to dryness to yield 0.52 g (82%) of (1R,5R,6S) 5-(1-ethyl-propoxy)-7-aza-bicyclo[4.1.0]hept-3-ene-3-carboxylic acid ethy as a yellow oil. IR (film): 3312, 2966, 2936, 2877, 1715, 1660, 1464, 1254, 1083, 1057, 799 cm$^{-1}$; MS (EI, 7o eV)): 253 (M$^+$), 224, 208, 182, 166, 110 m/z.

(d) Preparation of (3R,4R,5S)-4-acetylamino-5-allylamino-3-(1-ethyl-propoxy)-cyclohex-1-enecarboxylic acid ethyl ester In a 4 l 4-necked round bottom flask equipped with a thermometer, a mechanical stirrer, a Claisen condenser and an inert gas supply 278.0 g of (3R,4R,5S)-5-allylamino-4-amino-3-(1-ethyl-propoxy)-cyclohex-1-enecarboxylic acid ethyl ester obtained according to (c) were dissolved at room temperature with stirring under argon in 2800 ml of tert.-butyl methyl ether. From the red solution 1400 ml of tert.-butyl methyl ether were distilled. Again 1400 ml of tert.-butyl methyl ether were added and distilled off. The red solution was cooled to 0–5° C. and treated with 512 ml of acetic acid (9.0 mol) whereby the temperature rose to about 23° C. After cooling to 0° C.–5° C. 58.1 ml of methane-sulfonic acid (d=1.482, 0.90 mol) were added dropwise in the course of 27 min followed by 84.7 ml of acetic anhydride (d=1.08, 0.90 mol) added dropwise in the course of 40 min keeping the temperature in the range of 0° C. to 5° C. The brown reaction mixture was stirred without cooling for 14 h then treated with vigorous stirring with 1400 ml of water (deionized) for 30 min and the brown organic phase was extracted with 450 ml of 1M aqueous methanesulfonic acid. The combined aqueous phases (pH=1.6) were treated with stirring with about 694 ml of 50% aqueous potassium hydroxide until pH=10.0 was reached, keeping the temperature in the range of 10 to 25° C. The brown, turbid mixture was extracted first with 1000 ml then with 400 ml, in total with 1400 ml of tert.-butyl methyl ether, the combined organic extracts were stirred over 32 g of charcoal and filtered. The filter cake was washed with about 200 ml tert.-butyl methyl ether and the combined filtrates were evaporated in a rotary evaporator at 47° C./380 to 10 mbar to yield 285.4 g of brown-red, amorphous crystals which were dissolved with stirring in a mixture of 570 ml of tert.-butyl methyl ether and 285 ml of n-hexane at 50° C. The brown solution was cooled in 45 min with stirring to −20° C. to −25° C. and stirred for 5 h whereby brown crystals precipitated. The suspension was filtered over a pre-cooled (−20° C.) glass filter funnel and the filter cake was washed with a pre-cooled (−20° C.) mixture of 285 ml of tert.-butyl methyl ether and 143 ml of n-hexane and dried in a rotary evaporator at 48° C.<10 mbar to yield 200.33 g (83%) of (3R,4R,5S)-4-acetylamino-5-allylamino-3-(1-ethyl-propoxy)-cyclohex-1-enecarboxylic acid ethyl ester; m.p. 100.2° C.–104.2° C.

(e) Preparation of (3R,4R,5S)-4-acetylamino-5-amino-3-(1-ethyl-propoxy)-cyclohex-1-enecarboxylic acid ethyl ester In a 1 l 4-necked round bottom flask equipped with a thermometer, a mechanical stirrer, a reflux condenser and an inert gas supply 176.2 g of (3R,4R,5S)-4-acetylamino-5-allylamino-3-(1-ethyl-propoxy)-cyclohex-1-enecarboxylic acid ethyl ester obtained according to (d) and 30.0 ml of ethanolamine (d=1.015, 0.54 mol) were dissolved at room temperature in 880 ml of ethanol and treated with 17.6 g of 10% palladium on charcoal. The black suspension was heated to reflux for 3 h, cooled to room temperature and filtered. The filter cake was washed with 100 ml of ethanol and the combined filtrates were evaporated in a rotary evaporator at 50° C./<20 mbar. The brown, oily residue (207.3 g) was treated with 600 ml of 2N hydrochloric acid and the brown solution was distilled in a rotary evaporator at 50° C./75 mbar for 5 min. The solution was cooled to room temperature, washed with 600 ml of tert.-butyl methyl ether and treated with stirring and cooling with about 110 ml of 25% aqueous ammonia keeping the temperature below room temperature until pH=9–10 was reached and a brown emulsion formed. The emulsion was extracted three times with 600 ml, in total with 1800 ml of ethyl acetate. The combined extracts were dried over about 200 g of sodium sulfate and filtered. The filter cake was washed with about 200 ml of ethyl acetate and the combined filtrates were evaporated in a rotary evaporator at 50° C./<20 mbar to yield 158.6 g of a brown oil which was dissolved in 650 ml of ethanol. The brown solution was added in the course of 1 min with stirring to a hot solution (50° C.) of 57.60 g of 85% ortho-phosphoric acid (d=1.71, 0.50 mol) in 2500 ml of ethanol. The resulting solution was cooled in the course of 1 h to 22° C. At 40° C. seed crystals of (3R,4R,5S)-4-acetylamino-5-amino-3-(1-ethyl-propoxy)-cyclohex-1-enecarboxylic acid ethyl ester (about 10 mg) were added whereby crystallization started. The beige suspension was cooled in the course of 2 h to −20° C. to −25° C. and stirred at this temperature for 5 h. The suspension was filtered over a pre-cooled (−20° C.) glass filter funnel for 2 h. The filter cake was first washed with 200 ml of ethanol pre-cooled to −25° C., then twice with 850 ml, in total with 1700 ml acetone, then twice with 1000 ml, in total with 2000 ml of n-hexane, then dried at 50° C./20 mbar for 3 h to yield 124.9 g (70%) of (3R,4R,5S)-4-acetylamino-5-amino-3-(1-ethyl-propoxy)-cyclohex-1-ene carboxylic acid ethyl ester as white crystals; m.p. 205–207° C., decomposition.

EXAMPLE 2

Preparation of (3R,4R,5S)-5-amino-4-acetylamino-3-(1-ethyl-propoxy)-cyclohex-1-ene-carboxylic acid ethyl ester from (1S,5R,6R)-5-(1-ethyl-propoxy)-7-oxa-bicyclo[4.1.0]hept-3-ene-3-carboxylic acid ethyl ester Steps (a), (b), (d) and (e) were performed as described above in Example 1.

Step (c), preparation of (3R,4R,5S)-5-allylamino-4-amino-3-(1-ethyl-propoxy)-cyclohex-1-enecarboxylic acid ethyl ester from (3R,4S,5R)-5-amino-3-(1-ethyl-propoxy)-4-hydroxy-cyclohex-1-enecarboxylic acid ethyl ester, was carried out as set out below.

An autoclave with a 500 ml metal reactor equipped with a thermometer, a mechanical stirrer and an inert gas supply was charged under argon with 40.70 g of (3R,4S,5R)-5-amino-3-(1-ethyl-propoxy)-4-hydroxy-cyclohex-1- enecarboxylic acid ethyl ester (0.12 mol) obtained according to (b) and 200.0 ml of ethyl formate and the solution was heated with stirring to 100° C. at 4 to 5 bar in the course of 35 min, kept at this temperature for 6 h, then cooled to room temperature. The red solution was treated and evaporated twice with 150 ml, in total with 300 ml of toluene and evaporated at 45° C./300–15 mbar to yield as the crude intermediate 46.24 g of (3R,4R,5R)-5-formylamino-4-hydroxy-3-(1-ethyl-propoxy)-cyclohex-1-enecarboxylic acid ethyl ester as a red oil.

IR (film): 2967, 1715, 1385, 1247, 1100 cm$^{-1}$; MS (electron spray): 300 (M$^+$H$^+$), 270 (M$^-$COH), 253, 212, 138 m/z.

In a 1 l 4-necked round bottom flask equipped with a reflux condenser, a thermometer, a mechanical stirrer and an inert gas supply 46.24 g of the above crude intermediate (0.15 mol) were dissolved in 460 ml of ethyl acetate and 23.7 ml triethylamine (d=0.726, 0.17 mol). The orange solution was cooled to 0° C. to 5° C. and treated dropwise in the course of 30 min with 13.2 ml of methanesulfonyl chloride (d=1.452, 0.17 mol) during which time a white precipitate formed. After stirring for 60 min without cooling the suspension reached room temperature. After 45 min at room temperature the white suspension was filtered and the filter cake was washed with 45 ml of ethyl acetate. The combined filtrates were washed with 116 ml of 1M aqueous sodium bicarbonate solution, dried over 130 g of sodium sulfate, filtered and evaporated in a rotary evaporator at 45° C./180 to >10 mbar to yield as the crude intermediate 58.39 g of (3R,4R,5R)-5-formylamino-4-methanesulfonyloxy-3-(1-ethyl-propoxy)-cyclohex-1-enecarboxylic acid ethyl ester as an orange-red oil.

IR (film): 2967, 1715, 1358, 1177, 968 cm$^{-1}$; MS(EI, 70eV): 377(M), 290, 244, 148, 96 m/z.

In a 1 l 4-necked round bottom flask equipped with a reflux condenser, a thermometer, a mechanical and an inert gas supply 58.39 g of the above crude intermediate were dissolved in 290 ml of ethanol. The orange solution was treated with 10.7 ml of methanesulfonic acid (d=1.482, 0.17 mol) and heated to reflux for 160 min. The red-brown reaction was evaporated in a rotary evaporator at 45° C./190 to 30 mbar and the remaining red-brown oil was treated with 260 ml of deionized water and washed with 260 ml of tert.-butyl methyl ether. The organic phase was extracted with 52 ml of deionized water and the combined aqueous phases (pH=1.3) were cooled to 0° C. to 5° C. and treated with 13.7 ml of 50% aqueous potassium hydroxide keeping the temperature below 10° C. until pH=9.4 was reached whereby a beige emulsion formed. At a pH of 6.6 260 ml of ethyl acetate was added. The aqueous phase was extracted with 70 ml of ethyl acetate and the combined organic extracts were dried over 160 g of sodium sulfate, filtered and evaporated in a rotary evaporator at 45° C./190 to 20 mbar to yield as the crude intermediate 45.66 g of (3R,4R,5R)-5-amino-4-methansulfonyloxy-3-(1-ethyl-propoxy)-cyclohex-1-ene carboxylic acid ethyl ester as a red oil.

IR (film): 1720, 1362, 1250, 1170, 1070; MS(electronspray): 350, 3(M$^+$H$^+$), 290.3, 262.1, 202.2, 184.3 m/z.

An autoclave with a 500 ml glass reactor equipped with a thermometer, a mechanical stirrer and an inert gas supply was charged under argon with a red solution of 45.66 g (0.13 mol) of the crude intermediate above and 29.5 ml of allylamine (d=0.76, 0.39 mol) and 250 ml of ethyl acetate. The mixture was heated under 1 bar of argon with stirring to 111° C. to 112° C. in the course of 45 min, kept at this temperature at about 3.5 bar for 6 h, then cooled to room temperature in the course of 50 min. The orange suspension was vigorously stirred for 20 min with 230 ml of 1M aqueous sodium bicarbonate solution. The red brown organic phase was dried over 100 g of sodium sulfate and filtered. The filter cake was washed with about 50 ml of ethyl acetate and the combined filtrates were evaporated in a rotary evaporator at 45° C./160 to 10 mbar to yield as the crude intermediate 41.80 g of (3R,4R,5S)-5-allylamino-4-amino-3-(1-ethyl-propoxy)-cyclohex-1-ene carboxylic acid ethyl ester as a red oil.

IR (film): 3441, 1707, 1462, 1262, 1063 cm$^{-1}$; MS (electronspray): 311.2(M$^+$,H$^+$), 297.2, 266.3, 245.8, 223.2 m/z.

EXAMPLE 3

Preparation of trans-2-(allylamino)-cyclohexane amine from cyclohexene oxide (a) Preparation of trans-2-allylaminocyclohexanol In a 250 ml 2-necked round bottom flask equipped with a reflux condenser, a thermometer, a magnetic stirrer and an inert gas supply, 10.1 ml of cyclohexene oxide (100 mmol) were dissolved under argon at room temperature in 90 ml of tert.-butyl methyl ether and 10 ml of acetonitrile. Under stirring were added 5.16 g of magnesium bromide diethyl etherate (20 mmol) and 15 ml of allylamine (200 mmol). The yellowish solution was refluxed under argon during 4.5 h. After cooling to room temperature the reaction mixture was vigorously stirred with 50 ml of 5M aqueous ammonium chloride during 15 min. The aqueous phase was separated and extracted twice with 100 ml, in total with 200 ml tert.-butyl methyl ether. The combined organic phases were dried over 100 g sodium sulfate and the solvent was evaporated in a rotary evaporator (45° C./340–10 mbar) yielding 13.7 g of yellow-brown oil. The latter was shown by GC analysis to contain about 90% of racemic trans-2-allylaminocyclohexanol.

IR (film): 2928, 1450, 1071, 1030, 916 cm$^{-1}$; MS(EI, 70eV): 155(M$^+$), 112, 96, 83, 68 m/z.

(b) Preparation of trans-2-amino-cyclohexanol

In a 250 ml 2-necked round bottom flask equipped with a reflux condenser, magnetic stirrer and an inert gas supply, 13.6 g of racemic trans-2-allylaminocyclohexanol (0.87 mmol) obtained according to (a) were dissolved at room temperature in 140 ml ethanol and 2.88 g Pd/C 10% (66.1 mmol) were added to the solution. After refluxing during 2 h and cooling to room temperature, the black suspension was filtered through a glass fiber filter and the filter cake was washed with 60 ml of ethanol. The yellow solution was mixed with 2.55 ml sulfuric acid (d=1.83, 47.7 mmol), whereby a yellow precipitate was immediately formed. The solvent was removed in a rotary evaporator. The yellow-beige crystals were recrystallized in 75 ml of ethanol (0.5 h reflux, cooling to 0° C.). The white crystals obtained were washed with 60 ml of ethanol and dried in a rotary evaporator until reaching constant weight. 11.17 g of sulfate salt were obtained as white crystals.

This material was suspended in 110 ml of methanol and mixed with 13.6 ml of 5N sodium hydroxide methanol solution. The white suspension was stirred during 30 min at 55° C. The solvent was removed and the white crystals were suspended in 110 ml ethyl acetate. After adding about 4 g of sodium sulfate and 2 ml of water, the suspension was filtered and the crystals were dried in a rotary evaporator. About 7.28 g of white-beige crystals of racemic trans-2-amino-cyclohexanol were thus obtained, m.p. 65° C.–66° C.

(c) Preparation of trans-2-(benzylidenamino)-cyclohexanol

In a 250 ml round bottom flask equipped with a reflux condenser and a Dean-Stark trap, 6.91 g of racemic trans-2-aminocyclohexanol (60 mmol) obtained according to (b) were dissolved under argon in 70 ml of diisopropyl ether and 6.1 ml of benzaldehyde (60 mmol) were added to the solution which was refluxed under argon at 110° C. during 50 min until about 1 ml of water separated. The solvent was removed in a rotary evaporator (45° C./250–10 mbar) to obtain 12.11 g of white-beige crystals of racemic trans-2-(benzylidenamino)-cyclohexanol, m.p. 86° C.

(d) Preparation of trans-2-(benzylidenamino)-cyclohexyl methanesulfonic acid ester In a 250 ml round bottom flask equipped with a reflux condenser, 11.79 g racemic trans-2-(benzylidenamino)-cyclohexanol (58 mmol) obtained according to (d) were dissolved at room temperature under argon in 120 ml of ethyl acetate and 8.9 ml of triethylamine (63.8 mmol) were added. After cooling in an ice-bath 4.6 ml of methanesulfonyl chloride (58 mmol) were added to the solution during 6 min. The white solution obtained was stirred during 2.5 h, then mixed with 120 ml of 1M sodium hydrogen carbonate and stirred during 10 min. The two layers were separated and the aqueous phase was extracted twice with 120 ml of ethyl acetate. The combined organic phases were dried with 100 g of sodium sulfate and after filtration the solvent was removed in a rotary evaporator (45° C./240–10 mbar). The remaining yellow-orange crystals were suspended in 60 ml of n-hexane, the orange suspension was vigorously stirred for 15 min., filtered and washed with 20 ml of n-hexane. The crystals were dried in a rotary evaporator, added to the mother liquors and mixed with 30 ml of tert.-butyl methyl ether. The orange suspension was stirred vigorously during 15 min, the crystals were filtered off and dried in a rotary evaporator at 45° C./10 mbar to obtain 13.39 g of almost white crystals of racemic trans-2-(benzylidenamino)-cyclohexyl methanesulfonic acid ester, m.p. 94° C.

(e) Preparation of trans-2-(allylamino)-cyclohexylamine

In a 75 ml pressure reactor equipped with a magnetic stirrer, 4.16 g racemic trans-2-(benzylidenamino)-cyclohexyl methanesulfonic acid ester (14.7 mmol) obtained according to (d) were dissolved in 20 ml of acetonitrile and the white-yellow solution was mixed with 4.50 ml of allylamine (59.2 mmol). The closed system was heated during 20 h at 115° C., then cooled to 0° C. and the viscous solution concentrated. 20 ml of toluene and 22 ml 4N HCl (88.2 mmol) were added and the two-phase mixture was vigorously stirred during 2 h and the two phases were separated. The aqueous phase was extracted with 20 ml of toluene. To the aqueous phase, 7.9 ml 50% aqueous potassium hydroxide solution (102.9 mmol) were added with vigorous stirring and the mixture was extracted with 20 ml of toluene. The brown organic phase was dried with 10 g sodium sulfate, filtered and washed with 10 ml of toluene. The solvent was removed in a rotary evaporator (45° C./60–10 mbar). The product was purified by high-vacuum distillation on a Diekmann evaporator at 34° C.–36° C./0.25–0.3 mbar to obtain 0.95 g of racemic trans-2-(allylamino)-cyclohexylamine as white viscous liquid was thus obtained.

IR (film): 3340, 2940, 1450, 920, 758 cm$^{-1}$; MS (EI, 70eV): 155 (M), 125, 96, 70, 56 m/z.

EXAMPLE 4

Preparation of (S)-2-(N,N-diallylamino)-2-phenylethanol and (R)-2-(N,N-diallylamino)-1-phenylethanol In a 100 ml 2-necked flask equipped with a reflux condenser, a thermometer, a magnetic stirrer and an inert gas supply, 20 ml tetrahydrofuran were added to 2.3 ml (R)-phenyloxirane (20 mmol) and 1.03 g magnesium bromide ethyl etherate (4 mmol) were dissolved therein. The yellowish solution was mixed with 4.9 ml diallylamine and refluxed for 2 h. The orange-brown solution was cooled to room temperature, stirred for 15 min with 20 ml 5M ammonium chloride solution and the aqueous phase was separated. The organic phase was dried with 8.5 g sodium sulfate, filtered and washed with 10 ml tetrahydrofuran. The solvent was concentrated and the orange-brown oil was dried during 1 h to yield 4.2 g (97%) of (S)-2-(N,N-diallylamino)-2-phenylethanol and (R)-2-(N,N-diallylamino)-1-phenylethanol.

IR (film): 2820, 1640, 1452, 1062, 700 cm$^{-1}$; MS (electronspray): 218.3 (M+H$^+$), 200.2, 172.2, 158.2, 130.2 m/z.

EXAMPLE 5

Preparation of trans-2-((S)-methylbenzylamino)-cyclohexanol

In a 100 ml round bottom flask equipped with a reflux condenser, a thermometer, a magnetic stirrer and an inert gas supply, 4.6 ml of cyclohexene oxide (45 mmol) were dissolved under argon in 30 ml of tetrahydrofuran. The colorless solution was mixed under stirring with 1.17 g of magnesium bromide diethyl-etherate (4.5 mmol) and 3.6 ml of (S)-α-methylbenzylamine (30 mmol, 1 eq.). The weakly yellowish solution was refluxed under argon for 5.5 h, then cooled to room temperature, mixed with 30 ml of 5M ammonium chloride solution and 15 ml of 4M HCl (60 mmol, 2 eq.) and strongly agitated. 9 ml of a 25% aqueous ammonium hydroxide solution (120 mmol) were added and the two phases were separated after agitation. The organic phase was dried with 20 g sodium sulfate, filtered, washed with 20 ml tetrahydrofuran and concentrated in a rotary evaporator (45° C./357–10 mbar) yielding 7.47 g yellow oil. The latter was shown to contain a mixture of the two diastereoisomers A and B of trans-2-((S)-methylbenzylamino)-cyclohexanol separated by column chromatography (silica/tert.-butyl methyl ether+1% ammonia).

Data of diastereoisomer A: IR (film): 2928,2857, 1449, 1062, 761, 701 cm$^{-1}$; MS (electronspray): 220.4 (M$^+$, H$^+$), 174.2, 148.9, 116.2, 105.1 m/z.

Data of diastereoisomer B: IR (film): 2930, 2858, 1450, 1067, 762, 701 cm$^{-1}$; MS (electronspray): 220.3 (M$^+$H$^+$), 176.9, 159.2, 139.8, 116.2, 105.1 m/z.

EXAMPLE 6

Preparation of (3R,4S,5R)-5-benzylamino-3-(1-ethyl-propoxy)-4-hydroxy-cyclohex-1-enecarboxylic acid ethyl ester To a solution of 5.08 g (20 mmol) (1S,5R,6S)-5-(1-ethyl-propoxy)-7-oxa-bicyclo[4.1.0]hept-3-ene-3-carboxylic acid ethyl ester in 20 ml tetrahydrofuran 1.03 g (4 mmol) magnesium bromide diethyl etherate was added at room temperature. The resulting suspension was treated with 4.40 ml (40 mmol) of benzylamine and heated to reflux under argon with stirring for 12 hours. The reaction mixture was evaporated in a rotary evaporator, the residue treated with 20 ml of ethyl acetate and extracted 6 times with 20 ml of 5N aqueous ammonium chloride solution. The organic phase was dried over 5 g of sodium sulfate, filtered and evaporated to yield 6.88 g of (3R,4S,5R)-5-benzylamino-3-(1-ethyl-propoxy)-4-hydroxy-cyclohex-1-enecarboxylic acid ethyl ester as a brown oil.

IR (film): 2966, 2935, 2877, 1715, 1654, 1495, 1465, 1250, 1090, 976 cm$^{-1}$; MS (EI, 70 eV): 361 (M$^+$), 343, 330, 290, 274, 260, 242, 218, 200, 182, 166, 149, 138, 120, 106, 91 m/z.

EXAMPLE 7

Preparation of 2-allylamino-1-phenylethanol and 2-allylamino-2-phenylethanol

To a solution of 0.57 ml (5 mmol) 2-phenyl-oxirane in 5 ml tetrahydrofuran 0.26 g (1 mmol) magnesium bromide diethyl etherate was added at room temperature. The mixture was treated under argon with stirring with 0.56 ml (7.5 mmol) allylamine whereby a white suspension formed which dissolved after heating to 100° C. in a closed container. The yellow solution was heated at 100° C. for 2 hours, cooled to room temperature and stirred vigorously with 5 ml of 5N aqueous ammonium chloride solution for 10 minutes. The organic phase was separated, dried over 3 g of sodium sulfate, filtered and evaporated in a rotary evaporator. The oily residue containing the products was separated by chromatography on a silica gel column using tert.-butyl methyl ether containing 1% of conc. aqueous ammonia as the eluent to obtain 0.3 g of 2-allylamino-1-phenyl-ethanol (compound A) and 0.2 g 2-allylamino-2-phenyl-ethanol (compound B) as yellowish oils.

Data of compound A: IR (film): 1460, 1115, 1061, 919, 758, 701 cm$^{-1}$; MS (EI, 70 eV): 177 (M$^+$), 163, 146, 132, 117, 105, 97, 91, 83, 79, 77, 55, 43, 41 m/z.

Data of compound B: IR (film): 1500, 1460, 1049, 1027, 970, 759, 701 cm$^{-1}$; MS (70 eV): 146 (M$^+$–CH$_2$OH), 129, 117, 106, 104, 91, 77, 41 m/z.

EXAMPLE 8

Preparation of 3-(1-phenylethyl-amino)-butan-2-ol

To a solution of 0.445 ml (5 mmol) cis-2,3-dimethyl-oxirane in 5 ml tetrahydrofuran was added at room temperature 0.26 g (1 mmol) magnesium bromide diethyl etherate. The mixture was treated under argon with stirring with 0.67 ml (5.5 mmol) (S)-(–)-1-phenyl-ethylamine. The yellow suspension was heated at 90° C. in a closed container for 110 hours, whereby after 21 and 64 hours 0.25 ml and 0.122 ml respectively of cis-2,3-dimethyl-oxirane was added. The reaction mixture was cooled to room temperature and stirred vigorously with 5 ml of 5N aqueous ammonium chloride solution for 10 minutes. The organic phase was separated, dried over 2 g of sodium sulfate, filtered and evaporated in a rotary evaporator to obtain 0.58 g of 3-(1-phenyl-ethylamino)-butan-2-ol as a mixture of diastereoisomers as a brown oil. The oily residue was separated by chromatography on a silica gel column using ethyl acetate as the eluent to obtain the two diastereoisomers A and B as yellowish oils.

Data of diastereoisomer A: IR (film): 1451, 1180, 1053, 919, 759, 698 cm$^{-1}$; MS (electron spray): 194.3 (M$^+$+H), 216.3 (M$^-$+Na) m/z.

Data of diastereoisomer B: IR (film): 1458, 1075, 761, 700 cm$^{-1}$; MS (electron spray): 194.3 (M$^+$+H) m/z.

What is claimed is:

1. A process for preparing 1,2-diamino compounds of formula

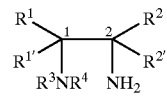

I and pharmaceutically acceptable addition salts thereof wherein R$^1$, R$^{1'}$, R$^2$ and R$^{2'}$, are, independently, H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, aryl-lower alkyl, aryl-lower alkenyl, or aryl-lower alkynyl, or R$^1$ and R$^2$, R$^1$ and R$^{2'}$, R$^{1'}$ and R$^2$ or R$^{1'}$ and R$^{2'}$ taken together with the two carbon atoms to which they are bound, are a carbocyclic or heterocyclic ring system, or R$^1$ and R$^{1'}$ or R$^2$ and R$^{2'}$ taken together with the carbon atom to which they are bound, are a carbocyclic or heterocyclic ring system, wherein at least one of R$^1$, R$^{1'}$, R$^2$ and R$^{2'}$ is not H, and R$^3$ and R$^4$, are, independently, H or a substituent of an amino group, wherein R$^3$ and R$^4$ are not both H, said process comprising the steps of a) reacting a 1,2-epoxide of formula

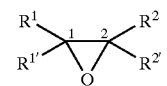

II wherein R$^1$, R$^{1'}$, R$^2$ and R$^{2'}$ are as above with an amine of formula R$^5$NHR$^6$ wherein R$^5$ and R$^6$, are, independently, H, or a substituent of an amino group, wherein R$^5$ and R$^6$ are not both H to form a 2-aminoalcohol of formula

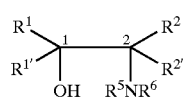

III wherein R$^1$, R$^{1'}$, R$^2$, R$^{2'}$, R$^5$ and R$^6$ are as above;

b) converting the the 2-aminoalcohol of formula (III) to the 2-aminoalcohol of formula

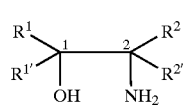

IV wherein R$^1$, R$^{1'}$, R$^2$ and R$^{2'}$ are as above;

c) transforming the 2-aminoalcohol of formula (IV) into a 1,2-diamino compound of formula

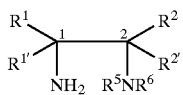

wherein $R^1$, $R^{1'}$, $R^2$, $R^{2'}$, $R^5$ and $R^6$ are as above;
wherein step (c) comprises the steps of:
(c1) protecting the free amino group of the 2-aminoalcohol of formula (IV) with a substituent of an amino group;
(c2) activating the hydroxy group into a leaving group, and
(c3) deprotecting the amino group and treating the reaction product with an amine of formula R5NHR6, wherein R5 and R6 are as above to form a 1,2-diamino compound of formula (V);
d) acylating the free amino group in position 1 of the 1,2-diamino compound of formula (V) to form an acylated 1,2-diamino compound of formula

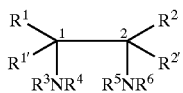

wherein $R^1$, $R^{1'}$, $R^2$ to $R^{2'}$, $R^3$, $R^4$, $R^5$ and $R^6$ are as above; and
e) deprotecting the amino group in position 2 of the 1,2-diamino compound of formula (VI) to produce the 1,2-diamino compound of formula (I).

2. The process of claim 1 wherein the 1,2 epoxide is a cyclohexane oxide of formula

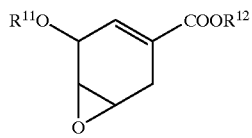

wherein $R^{11}$ and $R^{12}$ are as above.

3. The process of claim 2, wherein the cyclohexane oxide of formula (VIII) is (1S,5R,6R)-5-(1-ethyl-propoxy)-7-oxa-bicyclo[4.1.0]hept-3-ene-3-carboxylic acid ethyl ester.

4. The process of claim 1 wherein the 1,2 diamino compound is a 4,5-diamino-shikimic acid derivative of formula

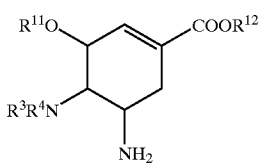

and pharmaceutically acceptable addition salts thereof, wherein
$R^{11}$ is an alkyl group or a substituted alkyl group, $R^{12}$ is an alkyl group and $R^3$ and $R^4$ are, independently, H or a substituent of an amino group, wherein $R^3$ and $R^4$ are not both H.

5. The process of claim 4, wherein the 4,5-diamino-shikimic acid derivative of formula (VII) is selected from the group consisting of (3R,4R,5S)-5-amino-4-acetylamino-3-(1-ethyl-propoxy)-cyclohex-1-ene-carboxylic acid ethyl ester, and (3R,4R,5S)-5-amino-4-acetylamino-3-(1-ethyl-propoxy)-cyclohex-1-ene-carboxylic acid ethyl ester phosphate (1:1).

6. The process of claim 1, wherein $R^5$ and $R^6$ in the amine of formula $R^5NHR^6$ are, independently, a straight chain or branched alkenyl of 2 to 6 C-atoms, benzyl, substituted benzyl, tri-substituted silyl methyl or heterocyclyl methyl.

7. The process of claim 6, wherein the amine of formula $R^5NHR^6$ is allylamine, diallylamine, benzylamine, dibenzylamine or trimethylsilyl amine.

8. The process of claim 7, wherein the amine of formula $R^5NHR^6$ is allylamine.

9. The process of claim 1, wherein the reaction of step (a) is conducted in the presence of a catalyst.

10. The process of claim 9, wherein the catalyst is a metal catalyst or a magnesium halide catalyst.

11. The process of claim 10, wherein the catalyst is magnesium bromide diethyl etherate.

12. The process of claim 1, wherein the conversion step (b) is performed at a temperature of from about 20° C. to about 150° C.

13. The process of claim 1, wherein the conversion step (b) is an isomerization/hydrolysis reaction performed in the presence of a metal catalyst wherein $R^5$ and $R^6$ are, independently, a straight chain or branched alkenyl of 2 to 6 C-atoms.

14. The process of claim 13, wherein the catalyst is a Pd/C catalyst.

15. The process of claim 13, wherein the isomerization/hydrolysis is performed in the presence of a primary amine.

16. The process of claim 15, wherein the primary amine is ethanolamine.

17. The process of claim 1, wherein the conversion in step (b) is a hydrogenolysis reaction performed with hydrogen in the presence of a metal catalyst wherein $R^5$ and $R^6$ are, independently, benzyl, substituted benzyl or heterocyclyl methyl.

18. The process of claim 1, wherein the conversion in step (b) is an oxidative cleavage reaction wherein $R^5$ and $R^6$ are, independently, a tri-substituted silyl methyl.

19. The process of claim 1 wherein step (c) comprises
(c1) protecting the free amino group of the 2-aminoalcohol of formula (IV) with a substituent of an amino group;
(c2) activating the hydroxy group into a leaving group, and
(c3) deprotecting the amino group and treating the reaction product with an amine of formula $R^5NHR^6$, wherein $R^5$ and $R^6$ are as above, to form the 1,2-diamino compound of formula (V).

20. The process of claim 19, wherein the substituted amino group in step (c1) is a Schiff base formed by reacting the 2-aminoalcohol of formula (IV) with a carbonyl group containing compound.

21. The process of claim 20, wherein the Schiff base is formed with benzaldehyde.

22. The process of claim 19, wherein the substituted amino group in step (c1) is an acyl group formed by reacting the 2-aminoalcohol of formula (IV) with an acylating agent.

23. The process of claim 19, wherein step (c2) comprises treating the hydroxy group with a sulfonylating agent to form a methane sulfonic acid ester leaving group.

24. The process of claim 23, wherein the sulfonylating agent is an anhydride of methane sulfonic acid or a halogenide of methane sulfonic acid.

25. The process of claim 19, wherein the amine of formula $R^5NHR^6$ is selected from the group consisting of allylamine, diallylamine, benzylamine, dibenzylamine and trimethylsilyl amine.

26. The process of claim 25 wherein the amine of formula $R^5NHR^6$ is allylamine.

27. The process of claim 1, wherein step (d) comprises treating the compound of formula (V) with an acetylating agent.

28. The process of claim 1, wherein the deprotecting step (e), is an isomerization/hydrolysis reaction performed in the presence of a metal catalyst, wherein $R^5$ and $R^6$ are, independently, a straight chain or branched alkenyl of 2 to 6 C-atoms.

29. The process of claim 28, wherein the metal catalyst is a Pd/C catalyst.

30. The process of claim 28, wherein the deprotecting step (e) is performed in the presence of a primary amine.

31. The process of claim 30, wherein the primary amine is ethanolamine.

32. The process of claim 1, wherein the deprotecting step (e) is a hydrogenolysis reaction performed with hydrogen in the presence of a metal catalyst wherein $R^5$ and $R^6$ are, independently, benzyl, substituted benzyl or heterocyclyl methyl.

33. The process of claim 1, wherein the deprotecting step (e) is an oxidative cleavage reaction wherein $R^5$ and $R^6$ are, independently, tri-substituted silyl methyl.

34. A process for preparing a 1,2-diamino compound of formula (V)

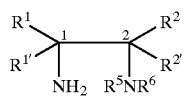

V wherein $R^1$, $R^{1'}$, $R^2$ and $R^{2'}$, are, independently, H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, aryl-lower alkyl, aryl-lower alkenyl, or aryl-lower alkynyl, or $R^1$ and $R^2$, $R^1$ and $R^{2'}$, $R^{1'}$ and $R^2$ or $R^{1'}$ and $R^{2'}$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, and $R^5$ and $R^6$, independently of each other, are H or a substituent of an amino group, wherein $R^5$ and $R^6$ are not both H, from a compound of the formula

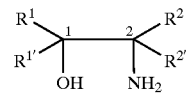

IV wherein $R^1$, $R^{1'}$, $R^2$, $R^{2'}$, $R^5$ and $R^6$ are as above comprising (a) protecting the free amino group of the 2-aminoalcohol of formula (IV) with a substituent of an amino group;

(b) activating the hydroxy group into a leaving group;

(c) deprotecting the amino group of the compound of formula (IV) to form an aziridine compound of the formula

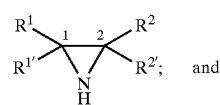

IX (d) reacting the aziridine compound of formula (IX) with an amine of formula $R^5NHR^6$, wherein $R^5$ and $R^6$ are as above to form the 1,2-diamino compound of formula (V).

35. The process of claim 34, wherein the amino group is a Schiff base formed by reacting the 2-aminoalcohol of formula (IV) with a carbonyl group containing compound.

36. The process of claim 35, wherein the Schiff base is formed with a benzaldehyde.

37. The process of claim 34, wherein the amino protecting group is an acyl group formed by reacting the 2-aminoalcohol of formula (IV) with an acylating agent.

38. The process of claim 34, wherein the leaving group is a sulfonic acid ester.

39. The process of claim 38 wherein the sulfonic acid ester is a methanesulfonic acid ester.

40. The process of claim 34 wherein the amine of formula $R^5NHR^6$ is allylamine, diallylamine, benzylamine, dibenzylamine or trimethylsilyl amine.

41. The process of claim 40 wherein the amine is allylamine.

* * * * *